US009017358B2

(12) United States Patent
Schwab et al.

(10) Patent No.: US 9,017,358 B2
(45) Date of Patent: Apr. 28, 2015

(54) ENDOSCOPIC TOOLS FOR THE REMOVAL OF BALLOON-LIKE INTRAGASTRIC DEVICES

(71) Applicant: Apollo Endosurgery, Inc., Austin, TX (US)

(72) Inventors: Justin J. Schwab, Santa Barbara, CA (US); Tiago Bertolote, Geneva (CH); Zachary P. Dominguez, Santa Barbara, CA (US); Mitchell H. Babkes, Santa Clarita, CA (US); Richard Law, Newbury Park, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 14/190,799

(22) Filed: Feb. 26, 2014

(65) Prior Publication Data
US 2014/0180327 A1   Jun. 26, 2014

Related U.S. Application Data (62) Division of application No. 13/372,171, filed on Feb. 13, 2012, now Pat. No. 8,882,798.

(51) Int. Cl.
*A61B 17/50* (2006.01)
*A61F 5/00* (2006.01)

(52) U.S. Cl.
CPC .............. *A61F 5/0089* (2013.01); *A61F 5/0036* (2013.01)

(58) Field of Classification Search
USPC ......... 606/108, 191–200; 623/1.1, 1.11, 1.12, 623/1.23
See application file for complete search history.

(56) References Cited

U.S. PATENT DOCUMENTS

| 4,416,267 | A | * | 11/1983 | Garren et al. | 128/898 |
| 4,598,699 | A | * | 7/1986 | Garren et al. | 606/185 |
| 4,694,827 | A | * | 9/1987 | Weiner et al. | 606/192 |
| 4,899,747 | A | * | 2/1990 | Garren et al. | 606/192 |
| 4,990,151 | A | * | 2/1991 | Wallsten | 606/108 |
| 5,002,556 | A | * | 3/1991 | Ishida et al. | 606/191 |
| 5,084,061 | A | * | 1/1992 | Gau et al. | 606/195 |
| 5,147,379 | A | * | 9/1992 | Sabbaghian et al. | 606/206 |
| 5,474,563 | A | * | 12/1995 | Myler et al. | 606/108 |
| 5,643,309 | A | * | 7/1997 | Myler et al. | 623/1.15 |
| 5,733,302 | A | * | 3/1998 | Myler et al. | 623/1.12 |
| 5,910,144 | A | * | 6/1999 | Hayashi | 606/108 |
| 5,941,895 | A | * | 8/1999 | Myler et al. | 606/195 |

(Continued)

FOREIGN PATENT DOCUMENTS

| DE | 8708978 | 11/1987 |
| EP | 0137878 A1 | 4/1985 |
| EP | 0695534 A2 | 2/1996 |

*Primary Examiner* — Ryan Severson
(74) *Attorney, Agent, or Firm* — Gordon & Jacobson, PC (57) ABSTRACT

A mechanism for removing a fluid-filled object such as an intragastric balloon from a patient. The apparatus includes a delivery tube having a lumen and a retrieval tool able to slide within the lumen that can both puncture and grasp the intragastric balloon. The retrieval tool may have sharpened graspers with either a sharp tip and/or knife-like edges. Alternatively, the delivery tube itself may have sharpened cutting blades that deploy outward to puncture the intragastric balloon. One embodiment utilizes a suction cup tip on the delivery sheath and a sharpened puncture rod that extends past the distal tip of the lumen, for rapid deflation of a balloon. Various embodiments hasten the deflation process and simplify the manipulation required by the surgeon.

14 Claims, 12 Drawing Sheets

(56) References Cited

U.S. PATENT DOCUMENTS

| | | | |
|---|---|---|---|
| 6,187,016 B1* | 2/2001 | Hedges et al. | 606/108 |
| 6,241,738 B1* | 6/2001 | Dereume | 606/108 |
| 6,251,122 B1* | 6/2001 | Tsukernik | 606/200 |
| 6,331,183 B1* | 12/2001 | Suon | 606/200 |
| 6,342,062 B1* | 1/2002 | Suon et al. | 606/200 |
| 6,558,404 B2* | 5/2003 | Tsukernik | 606/198 |
| 6,673,100 B2* | 1/2004 | Diaz et al. | 623/1.11 |
| 6,676,692 B2* | 1/2004 | Rabkin et al. | 623/1.11 |
| 6,802,846 B2* | 10/2004 | Hauschild et al. | 606/110 |
| 6,837,901 B2* | 1/2005 | Rabkin et al. | 623/1.11 |
| 7,041,117 B2* | 5/2006 | Suon et al. | 606/200 |
| 7,201,768 B2* | 4/2007 | Diaz et al. | 623/1.11 |
| 7,258,696 B2* | 8/2007 | Rabkin et al. | 623/1.11 |
| 8,025,668 B2* | 9/2011 | McCartney | 606/106 |
| 8,038,704 B2* | 10/2011 | Sherburne | 623/1.11 |
| 8,287,551 B2* | 10/2012 | McCartney | 606/106 |
| 8,470,016 B2* | 6/2013 | Sherburne | 623/1.11 |
| 8,882,798 B2* | 11/2014 | Schwab et al. | 606/205 |
| 2001/0023358 A1* | 9/2001 | Tsukernik | 606/200 |
| 2002/0055757 A1* | 5/2002 | Torre et al. | 606/192 |
| 2002/0120277 A1* | 8/2002 | Hauschild et al. | 606/108 |
| 2002/0161377 A1* | 10/2002 | Rabkin | 606/108 |
| 2002/0161427 A1* | 10/2002 | Rabkin et al. | 623/1.11 |
| 2004/0087965 A1* | 5/2004 | Levine et al. | 606/108 |
| 2004/0106932 A1* | 6/2004 | Diaz et al. | 606/108 |
| 2004/0147939 A1* | 7/2004 | Rabkin et al. | 606/108 |
| 2005/0080431 A1* | 4/2005 | Levine et al. | 606/108 |
| 2005/0192615 A1* | 9/2005 | Torre et al. | 606/192 |
| 2006/0155310 A1* | 7/2006 | Binmoeller | 606/151 |
| 2008/0208135 A1* | 8/2008 | Annunziata | 604/175 |
| 2008/0208239 A1* | 8/2008 | Annunziata | 606/191 |
| 2008/0208241 A1* | 8/2008 | Weiner et al. | 606/192 |
| 2008/0249566 A1* | 10/2008 | Harris et al. | 606/220 |
| 2008/0269555 A1* | 10/2008 | Paganon et al. | 600/104 |
| 2009/0093838 A1* | 4/2009 | Paganon | 606/192 |
| 2009/0157115 A1* | 6/2009 | Fleming | 606/200 |
| 2010/0234853 A1* | 9/2010 | Pecor et al. | 606/108 |
| 2011/0276121 A1* | 11/2011 | Levine | 623/1.12 |
| 2012/0022580 A1* | 1/2012 | McCartney | 606/200 |
| 2013/0211440 A1* | 8/2013 | Schwab et al. | 606/192 |
| 2013/0289694 A1* | 10/2013 | Sherburne | 623/1.11 |
| 2014/0180327 A1* | 6/2014 | Schwab et al. | 606/192 |

* cited by examiner

ENDOSCOPIC TOOLS FOR THE REMOVAL OF BALLOON-LIKE INTRAGASTRIC DEVICES

FIELD OF THE INVENTION

The present invention relates, in general, to the use of intragastric balloons and similar fluid-filled objects used in the treatment of obesity and, in particular to devices and methods for removing or retrieving such intragastric balloons and/or other fluid-filled objects from the stomachs of patients.

BACKGROUND OF THE INVENTION

Intragastric balloons or other balloons and objects commercially available are designed for providing short-term therapy for moderately obese individuals who need to shed pounds in preparation for surgery or as part of a dietary and behavioral modification program. One such inflatable intragastric balloon is described in U.S. Pat. No. 5,084,061 and is commercially available as the Orbera® System from Allergan Medical of Irvine, Calif. Clinical results with these devices show that for many obese patients, the intragastric balloons significantly help to control appetite and accomplish weight loss.

The Orbera® System, for example, consists of a silicone elastomer intragastric balloon that is inserted into the stomach in an empty or deflated state and thereafter filled (fully or partially) with a suitable fluid. The balloon occupies space in the stomach, thereby leaving less room for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Intragastric balloons typically are implanted for a finite period of time, up to six months. This time period may be shortened by a treating physician who wishes to alter the patient's treatment and remove the balloon prior to the six month period. In any event, at some point after the balloon has been endoscopically placed in the stomach, it will become desirable to remove the balloon from the stomach. The usual means of removing the balloon is to deflate it by puncturing the balloon, and either aspirating the contents of the balloon or allowing the fluid to pass into the patient's stomach. This means of removing saline from the balloon requires surgical intervention, through the use of a gastroscopic instrument. When the balloon is deflated in this manner, the balloon itself may be surgically removed using the gastroscopic instrument.

Those experienced in the art will readily appreciate that manipulating the balloon in situ in order to deflate the balloon can be difficult. This is because the balloon is slippery and positionally unstable. The usually spherical or ellipsoidal intragastric balloons may readily rotate in the stomach, making it difficult for a surgeon to manipulate the balloon in order to find a deflation valve, or to safely puncture the balloon using a surgical instrument. One technique for addressing this issue is described in U.S. Pat. No. 5,084,061 and includes providing a retrieval tab on the outer surface of the balloon. A tool with a hook, loop, or snare then has to be latched onto the tab to stabilize, and assist in deflation and retrieval of the balloon. This technique has not been widely adopted as it requires specially manufactured balloons or objects with the external tab. This configuration also requires that the balloon be manipulated within the patient's stomach to find and align the tab with the hook on the removal tool, which is often difficult to perform endoscopically (e.g., with limited tool dexterity and in limited visibility and light provided by the endoscope).

Also, current removal procedures typically require the use of multiple endoscopic instruments in order to first aspirate or puncture the balloon, and then to grasp the balloon for removal from the body. Further, current balloon removal technology requires the surgeon to target and puncture the balloon with a common aspirating needle, creating a pinhole through the shell of the balloon, which enables drainage. However, the size of this pinhole necessitates multiple punctures to be made, and occasional assistance from the physician to forcefully squeeze the balloon using the endoscope in order to drain the device (common with saline filled balloons).

Hence, there remains a need for an improved tool for deflation and retrieval of intragastric balloons and other fluid-filled objects from the stomach of patients. Preferably, such a tool would be useful with existing medical systems or tools such as endoscopes and would provide quicker and more effective grasping or capture of the balloon.

SUMMARY OF THE INVENTION

The present invention addresses the above-described problems by providing apparatuses and methods for removing a fluid-filled object such as an intragastric balloon from a patient. The apparatus includes a delivery tube having a lumen and a retrieval tool able to slide within the lumen that can both puncture and grasp the intragastric balloon. The retrieval tool may have sharpened graspers with either a sharp tip and/or knife-like edges. Alternatively, the delivery tube itself may have sharpened cutting blades that deploy outward to puncture the intragastric balloon. One embodiment utilizes a suction cup tip on the delivery sheath and a sharpened puncture rod that extends past the distal tip of the lumen, for rapid deflation of a balloon. Various embodiments hasten the deflation process and simplify the manipulation required by the surgeon.

On exemplary embodiment includes a system for retrieving an intragastric balloon comprising an elongated delivery tube having a lumen. A balloon retrieval tool is disposed and able to slide within the delivery tube lumen and has a pair of grasper arms and a pair of cutter arms, both of which may be displaced longitudinally within the lumen of the delivery tube. Both of the pairs of arms are pre-formed to have bends such that they diverge outward upon being expelled from the distal end of the delivery tube, the grasper arms being longer than the cutter arms, and emerge from the delivery tube first. The grasper arms have grasping hooks on the distal ends thereof and the cutter arms have hooks that are sharper than the grasper arms to facilitate piercing of an intragastric balloon. The hooks of the grasper arms are each desirably bent between 100-135° relative to the adjacent segment of the grasper arm, preferably about 120° relative to the adjacent segment of the grasper arm.

A further system for retrieving an intragastric balloon disclosed herein comprises an elongated delivery tube having a lumen, and a balloon retrieval tool disposed and able to slide within the delivery tube lumen, the retrieval tool having a pair of grasping arms advanced slightly past a pair of cutting arms. Each grasping arm has a relatively straight axially-oriented proximal section separated from a distal segment at a bend, and the terminal end of each of the grasping arms has a grasping hook facing the hook of the other grasping arm. Each cutting arm has a relatively straight axially-oriented proximal section separated from a distal segment at a bend, and each distal segment further includes an outwardly bent portion that terminates at distal cutting hooks, wherein the inside edges of the outwardly bent portions are sharp to enable cutting of the shell of the intragastric balloon.

In accordance with another aspect, the present application provides a system for retrieving an intragastric balloon comprising an elongated delivery tube having a lumen and a balloon retrieval tool disposed and able to slide within the delivery tube lumen. The retrieval tool has a pair of identical grasping arms formed of a flexible material, wherein a distal segment of each grasping arm diverges away from the other grasping arm when expelled from the delivery tube. Each arm terminates in a hook that is bent inward toward the hook of the other arm, and the hooks are sharpened on their outer curvatures to enable piercing an intragastric balloon when pushed into the side thereof. The tips of the hooks are desirably relatively dull to facilitate grasping and pulling the deflated balloon rather than piercing of it. Preferably, the hooks are bent between 100-135° relative to the adjacent segment of the grasping arm, such as about 120°. Each of the grasping arms preferably includes a length of the distal segment that is sharpened, such as having a sharpened knife edge projecting outward, or facing away from the other arm.

Another embodiment of a system for retrieving an intragastric balloon comprises an elongated delivery tube having a lumen, and a balloon retrieval tool disposed and able to slide within the delivery tube lumen. The retrieval tool has a pair of arms that are strategically bent to open and close at relative tool/delivery tube positions. Namely, each arm includes a straight elongated proximal portion leading to a gradually divergent bend or arc which terminates at an outward elbow, and each arm subsequently changes direction for a short distance along a crossover portion, reversing positions with the other arm, and wherein a distal segment extends from the crossover portion to a distal hook facing the hook of the other arm.

A further aspect of the application is a system for retrieving an intragastric balloon comprising a balloon retrieval tool having a pair of articulated grasping jaws and actuating pull wires to open and close the jaws. An elongated delivery tube has a lumen for receiving the retrieval tool, the delivery tube having a distal sheath portion with a pair of flexible cutting blades formed in an outer wall thereof which may be bent outward by opening the grasping jaws.

Another system for retrieving an intragastric balloon described herein comprises an elongated delivery tube having a lumen, and a balloon retrieval tool disposed and able to slide within the delivery tube lumen. The retrieval tool having an elongated shaft terminating at a distal corkscrew-like member having a pointed end designed to puncture an intragastric balloon and a coiled body.

A still further system for retrieving an intragastric balloon comprises an elongated delivery tube having a lumen and terminating in a suction cup. A balloon retrieval tool is disposed and able to slide within the delivery tube lumen, and comprises an elongated piercing rod that extends through the lumen of the delivery tube and terminates in a sharpened tip.

Finally, another system for retrieving an intragastric balloon comprises an elongated delivery tube having a lumen and terminating in a sharp distal end. A balloon retrieval tool disposed and able to slide within the delivery tube lumen comprises a wireform that is preformed so as to curl back on itself when expelled from the delivery tube and having a sharp distal tip.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention is directed to methods and devices for the removal of fluid filled (air, water, saline, etc.) intragastric balloons. As mentioned above, current removal procedures possess inefficiencies and complexities which increase procedure duration, and risk to the patient. For instance, current balloon removal graspers are essentially of a fish-hook design, which prevents release of the deflated balloon shell once fully grasped with the tool. This may have the benefit of helping to prevent unintentional releases while removing a device from a patient, yet also removes control from the physician.

Figure 1:
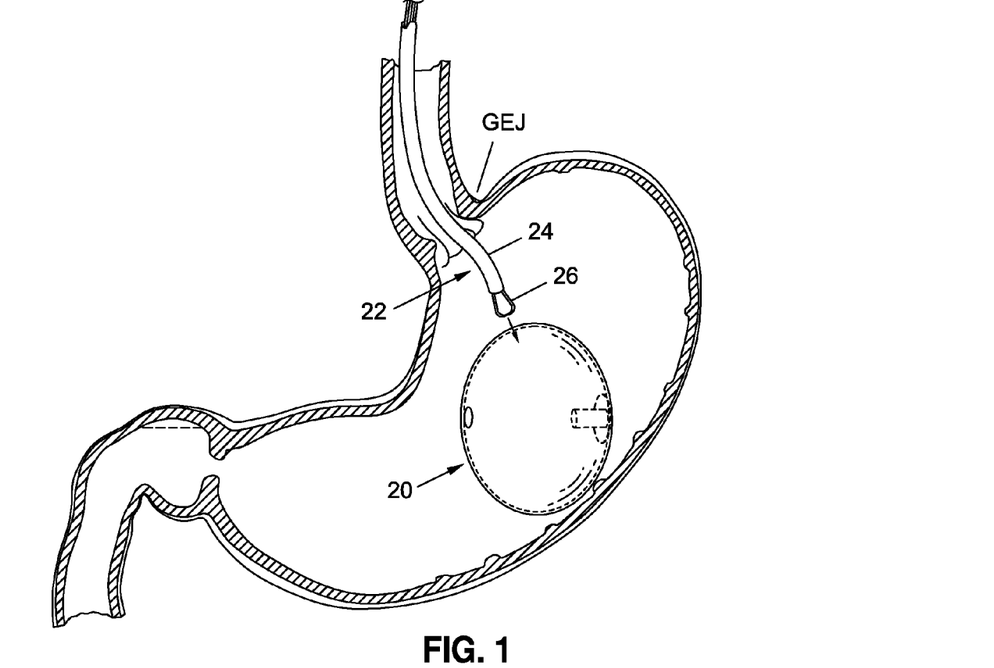
FIG. 1 is sectional view along a longitudinal mid-plane of the stomach showing an inflated intragastric balloon implanted therein and an exemplary balloon retrieval system advanced into proximity therewith.

FIG. 1 is sectional view along a longitudinal mid-plane of the stomach showing an inflated intragastric balloon 20 implanted therein and an exemplary balloon retrieval system 22 advanced into proximity therewith. The balloon retrieval system 22 comprises an elongated delivery sheath or tube 24 having an internal lumen through which a balloon retrieval tool 26 slides. The retrieval tool lumen 22 typically operates through an instrument channel of a standard endoscope (not shown). FIG. 1 shows the tube 24 advanced through the gastroesophageal junction GEJ so that a distal end 28 thereof is positioned a short distance away from the balloon 20. The positioning of the tube 24 and subsequent deployment of the tool 26 are desirably guided by visualization through an endoscope (not shown).

Figure 2A:
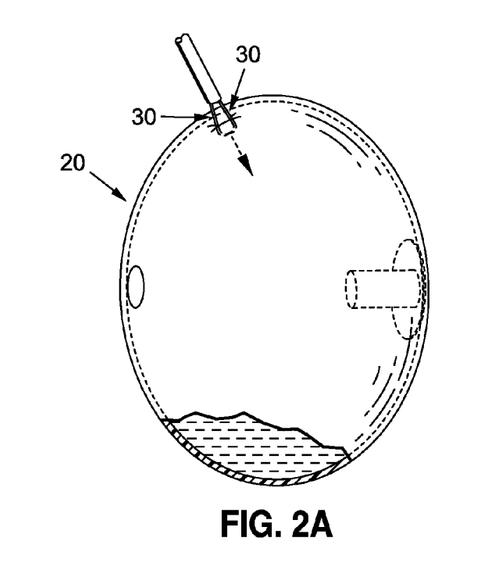
FIGS. 2A-2B are perspective views of the intragastric balloon and the exemplary balloon retrieval system of FIG. 1 with a retrieval tool shown first advancing and puncturing and then retreating and cutting the balloon.
Figure 2B:
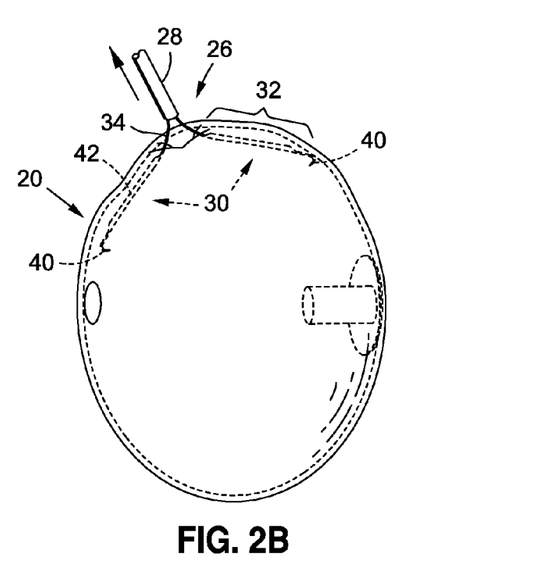

FIGS. 2A-2B are enlarged perspective views of the exemplary balloon retrieval system 22 of FIG. 1 with the retrieval tool 26 extended and just prior to and after engagement with the balloon 20. The retrieval tool 26 includes a pair of identical grasping arms 30 that are formed of a flexible material such as stainless steel or Nitinol. A distal segment 32 of each grasping arm 30 diverges away from the other grasping arm when expelled from the delivery tube 24. For example, the distal segments 32 commence at bends 34 pre-formed in the grasping arms 30. When pulled into the delivery tube 24, the bends 34 straighten out such that the distal segments 32 aligned with the proximal portion of the grasping arms 30. In a preferred embodiment, the distal end 28 of the delivery tube 24 is flared slightly such that the grasping arms 30 can fully retract therein.

Each of the grasping arms 30 terminates in hooks 40 that are bent inward toward the other hook. The hooks 40 are sharpened on their outer curvatures to enable piercing of the intragastric balloon 20 when pushed into the side thereof, as indicated in FIG. 2A. The tips of the hooks 40, in contrast, are relatively dull to facilitate grasping and pulling the deflated balloon 20. In contrast to grasping arms of the prior art, the hooks 40 are bent between 100-135°, and preferably about 120°, relative to the adjacent segment of the grasping arm to facilitate detachment and repositioning of the hooks if necessary. That is, typical grasping arms have hooks that are bent approximately 180°, which helps prevent inadvertent detachment but at the same time makes deliberate detachment and repositioning difficult.

The exemplary balloon retrieval tool 26 combines fluid drainage via cutting, and removal of the device via grasping. More particularly, each of the grasping arms 30 includes a length of the distal segment 32 that is sharpened. In a preferred embodiment, both of the distal segments 32 have a sharpened knife edge 42 projecting outward, or facing away from the other arm. This permits cutting of the intragastric balloon 20 after the hooks 40 have pierced the balloon, such as during retraction as seen in FIG. 2B. Alternatively, the sharpened knife edge 42 may be formed on the inside of the distal segment 32, or facing toward the other arm, or in another direction that facilitates cutting of the shell of the balloon 20. More particularly, providing the knife edges 42 allows a slit to be cut in the shell of the balloon 20, as opposed to a small puncture from just a hook or needle. The slit permits the fluid (e.g., saline) within the balloon to drain much faster than through a puncture, and obviates the need for multiple punctures.

The balloon retrieval system 22 of FIGS. 1 and 2 operates using a three-step procedure. First, the retrieval tool 26 is pushed from the protective tube 24 such that the grasping hooks 40 are exposed. The surgeon presses the leading sharp convex curvature of the hooks 40 against the shell of the intragastric balloon 20 (FIG. 2A). Due to the sharpened hooks 40, the tool 26 punctures and penetrates the interior of the balloon shell. Subsequently, the surgeon pushes the retrieval tool 26 fully into the interior of the balloon shell, and fully extends the tool from the delivery tube 24, thus causing the grasping arms 30 to diverge. By manually pulling the grasping tool 26 from the interior to the exterior, the sharpened arms 30 (or reverse scissors) cut the shell and allow quick drainage of the implant (FIG. 2B). Grasping of the shell is then accomplished using standard grasper techniques with the dull points of the hooks 40.

Figures 3A, 3B:
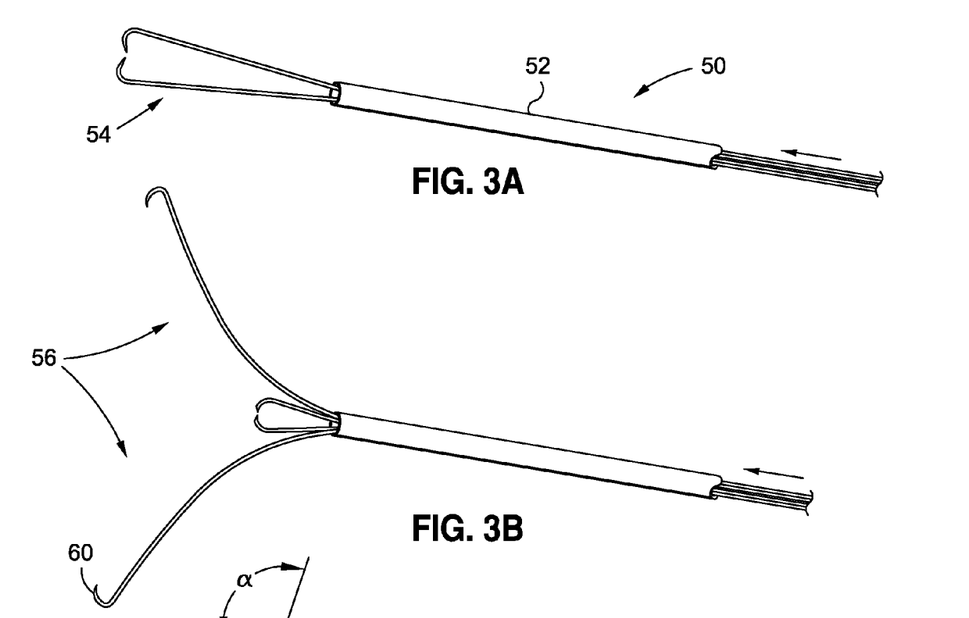
FIGS. 3A-3C are perspective views of a distal end of an exemplary dual-wire balloon retrieval tool in several progressive stages of deployment.
Figure 3C:
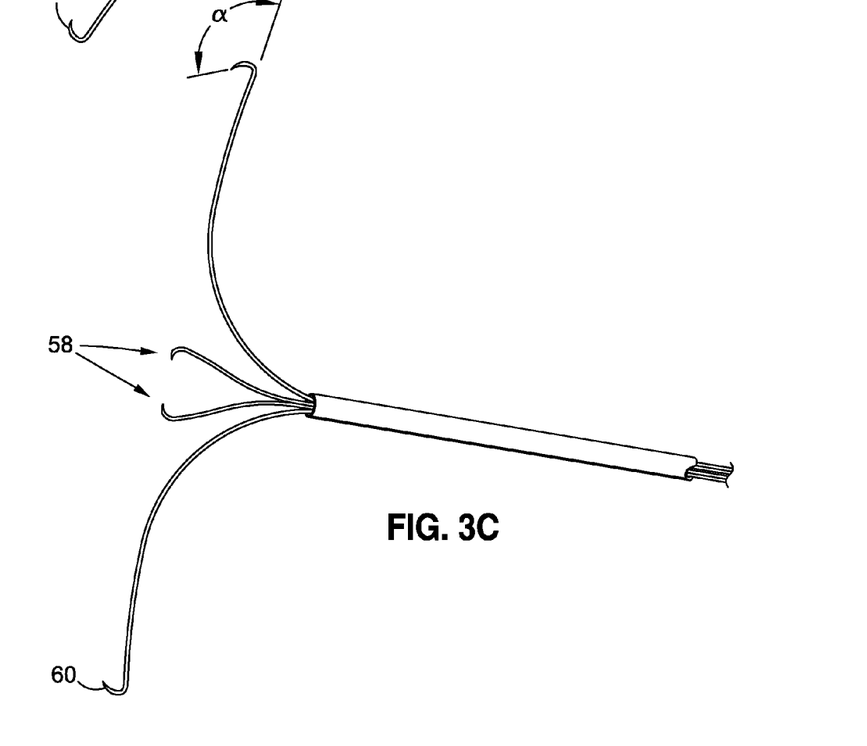

FIGS. 3A-3C are perspective views of a distal end of an exemplary dual-wire pair balloon retrieval system 50 in several progressive stages of deployment. The system 50 includes a delivery tube 52, much like that described above, and a dual-wire pair balloon retrieval tool 54. The retrieval tool 54 includes a pair of grasper arms 56 and a pair of cutter arms 58, both of which may be displaced longitudinally within the lumen of the delivery tube 52. As with the embodiment described above, both of the pairs of arms 56, 58 are pre-formed to have bends such that they diverge outward upon being expelled from the distal end of the delivery tube 52. The grasper arms 56 are longer than the cutter arms 58, and emerge from the delivery tube 52 first. The grasper arms 56 include grasping hooks 60 on the distal ends thereof. In FIG. 3A, distal portions of the grasper arms 56 are seen projecting from the end of the delivery tube 52. FIG. 3B shows the arms displaced farther distally through the tube 52 such that the grasper arms 56 begin to spread apart and the cutter arms 58 are visible. Finally, FIG. 3C shows the arms fully extended with the grasper arms 56 spread wide and the cutter arms 58 also spread apart a minimum distance.

Figure 4A:
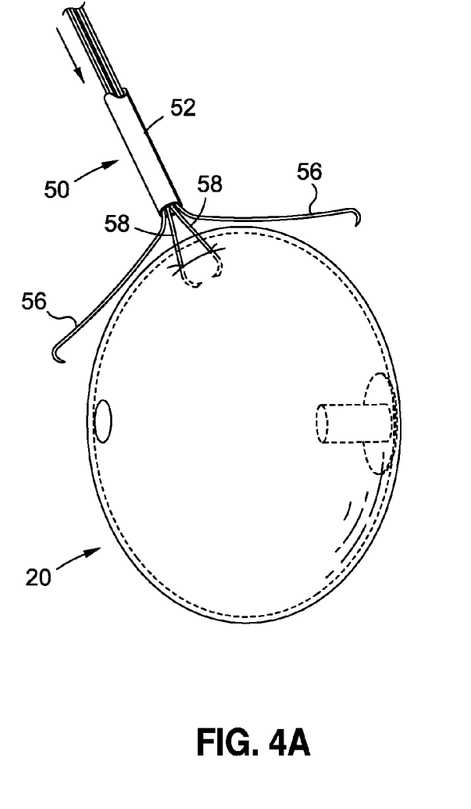
FIGS. 4A-4B are perspective views showing engagement of the balloon retrieval tool of FIGS. 3A-3C with the intragastric balloon to effect deflation and removal thereof.
Figure 4B:
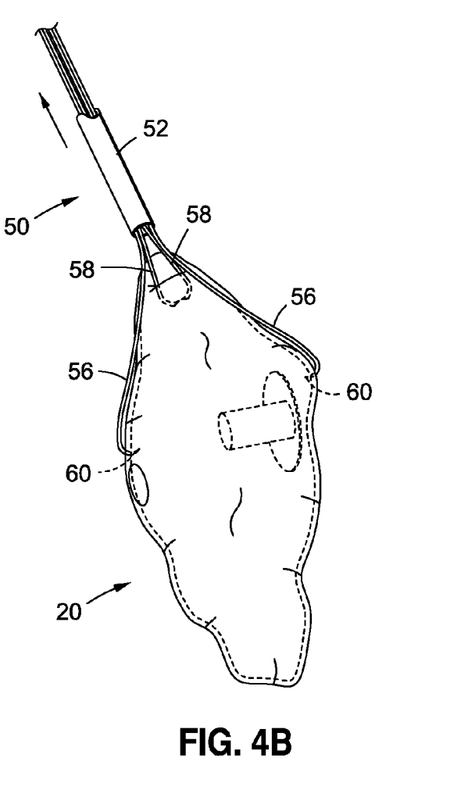

FIGS. 4A-4B are perspective views showing engagement of the balloon retrieval system 50 with the intragastric balloon 20 to affect deflation and removal thereof. The system 50 operates using a three-step procedure. First, the surgeon pushes the grasper 56 and cutter 58 arms from the protective sheath 52, so that the cutter arms 58 can purchase part of the balloon shell, and the grasper arms 56 are wide enough apart to prevent premature grasping. In this manner, the instrument can be treated as a standard endoscopic grasper. In this step, the grasper arms 56 open wide enough to allow the cutter arms 58 to press against the shell of the intragastric balloon 20. Finally, the grasper arms 56 and cutter arms 58 are retracted within the instrument lumen, which causes the cutter arms 58 to cut a slit in the shell of the balloon 20 and the grasper arms 56 to grasp the balloon 20 for removal. FIG. 4B illustrates the simultaneous cutting motion of the cutter arms 58, and the grasping arms 56 of the embodiment described. As the wire pairs are retracted into their instrument lumen 52, the cutters by design would collapse quicker and create a cut in the balloon increasing balloon deflation time, while the grasping arms 56 close down on the balloon shell for grasping and retrieval.

As mentioned above, the grasping hooks 60 are desirably bent at an angle $\alpha$ of between 100-135°, as seen in FIG. 3C. This geometry provides the ability to grasp the intragastric balloon 20 at relatively wide grasping angles, in contrast to earlier hooks which are bent 180°. Additionally, this geometry allows for cutting features to be placed on the inside bend diameter of the instrument. The grasping hooks 60 may alternatively be bent 90° to enable easier release and repositioning of the hooks, but at the expense of holding force. Like the 135° degree bend, a 90° geometry could also include additional cutting features. It should be noted that the length of a 90° bent grasping tip affects holding power, and must be sized to fit within the instrument lumen.

Figure 5A:
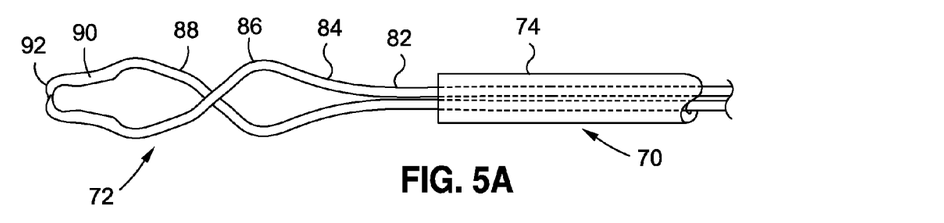
FIGS. 5A-5C are elevational views of a distal end of an alternative balloon retrieval system having a scissor-like balloon retrieval tool in several progressive stages of deployment.
Figure 5B:
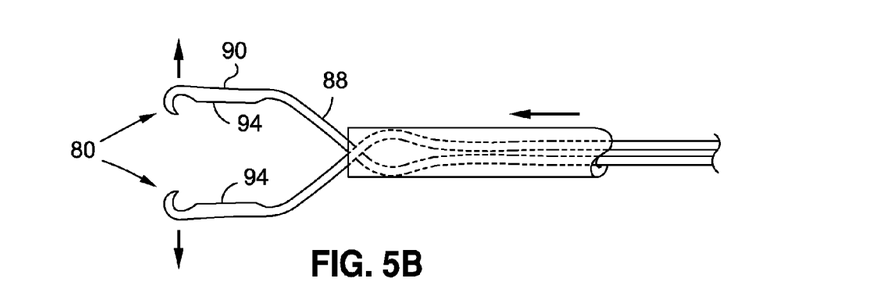
Figure 5C:
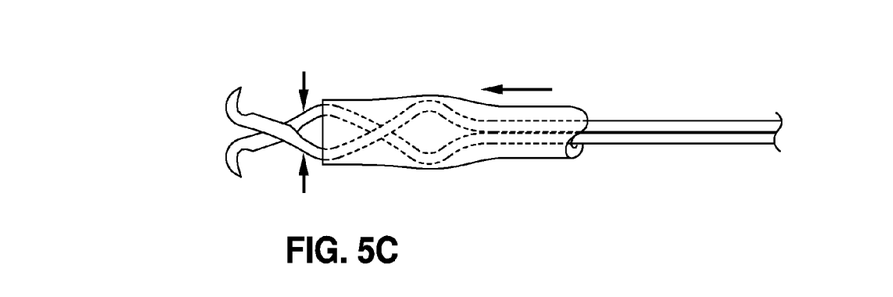
Figure 6A:
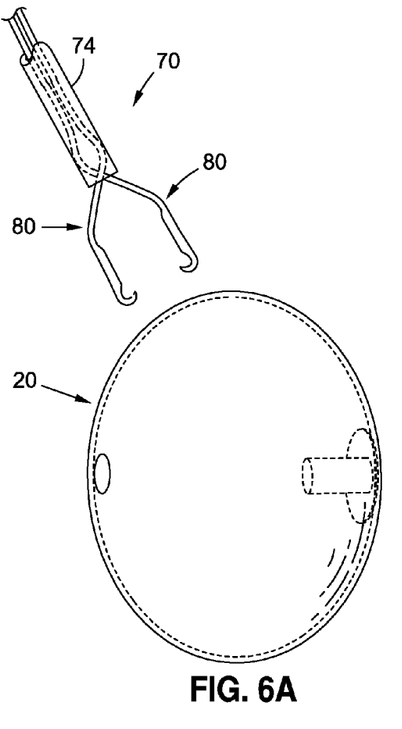
FIGS. 6A-6C are perspective views showing engagement of the balloon retrieval tool of FIGS. 5A-5C with an intragastric balloon to effect deflation and removal thereof.
Figures 6B, 6C:
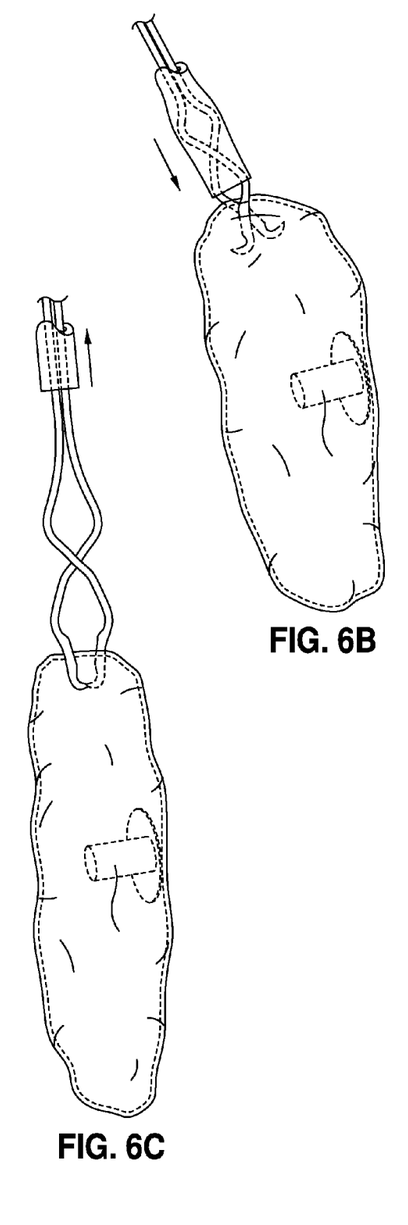

FIGS. 5A-5C are elevational views of a distal end of an alternative balloon retrieval system 70 having a scissor-like balloon retrieval tool 72 that slides through a delivery tube 74 in several progressive stages of deployment. FIG. 5A shows the balloon retrieval tool 72 in a closed orientation, FIG. 5B illustrates distal displacement of the delivery tube 74 to place the retrieval tool 72 in an open orientation, and FIG. 5C show still further delivery tube 74 advancement such that the retrieval tool 72 converts to a fully retracted, shell cutting orientation. FIGS. 6A-6C are perspective views showing engagement of the balloon retrieval system 70 of FIGS. 5A-5C with the intragastric balloon 20 to effect deflation and removal thereof. FIG. 6A shows the neutral wireform position upon instrumentation approach to the intragastric balloon; FIG. 6B illustrates the wireform scissor-like cut operation performed by retracting the wireform into the lumen 74 of the instrument to affect deflation of the balloon; FIG. 6C illustrates the grasping operation performed by pushing the wireform completely from the lumen 74 of the instrument to affect retrieval of the balloon.

The retrieval tool 72 comprises a pair of arms 80 that are strategically bent to open and close at relative tool/delivery tube 74 positions. Each arm 80 includes a straight elongated proximal portion 82 leading to a gradually divergent bend or arc 84. The arc 84 terminates at an outward elbow 86. From there, each arm 80 changes direction for a short distance along a crossover portion 88, so named because it crosses from one diametric side of the tool to the other, reversing positions with the other arm. Finally, a distal segment 90 extends from the crossover portion 88 to a distal hook 92. In use, distal displacement of the delivery tube 74 first cams the elbows 86 inward toward each other which causes the crossover portion 88 and distal segments 90 to spread apart, as seen in FIG. 5B. Further displacement of the delivery tube 74 as seen in FIG. 5C acts on the crossover portions 88 to cause the distal segments 90 to converge toward each other and preferably to cross over one another.

The balloon retrieval system 70 operates using a three-step procedure. First, when the retrieval tool 72 is fully exposed it stays closed, as seen in FIG. 5A. This default configuration allows the operator to grasp the device for manipulation, and/or removal from the body. The amount of force the graspers have when closed is proportional to the size of the wire, material of choice, and bending geometry. Subsequently, when the retrieval tool 72 is retracted into the instrument lumen to the middle position of FIG. 5B, the grasper jaws comprising the distal segments 90 and distal hooks 92 spread apart. This imitates standard grasping forceps. Desirably, the distal segments 90 have sharpened edges 94 on the inside surfaces, and sharpened grasping points on the end of the hooks 92. When the retrieval tool 72 fully retracts within the instrument lumen, or vice versa the delivery tube 74 is displaced distally relative to the tool, the sharp points of the hooks 92 and sharp edges 94 are able to collapse and cut/tear the intragastric balloon-like shell. In this manner, the device provides cutting, and grasping functionality within a single instrument.

Figure 7A:
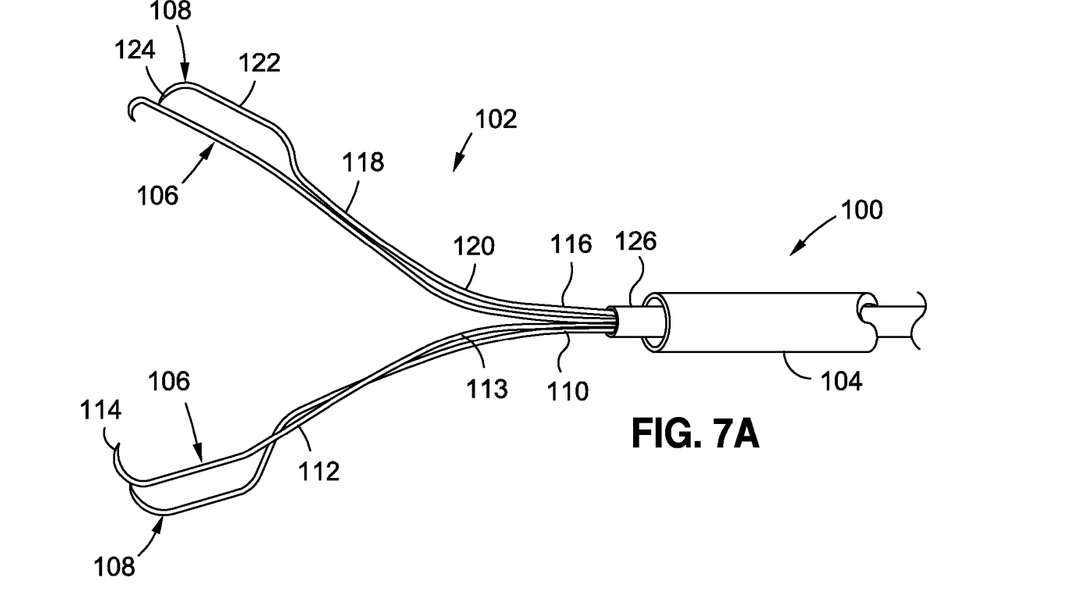
FIGS. 7A-7C are elevational views of a distal end of an alternative balloon retrieval system with a multi-wire balloon retrieval tool in several progressive stages of deployment.
Figure 7B:
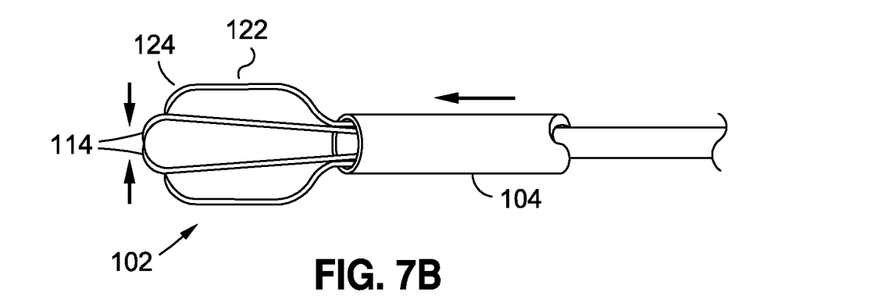
Figure 7C:
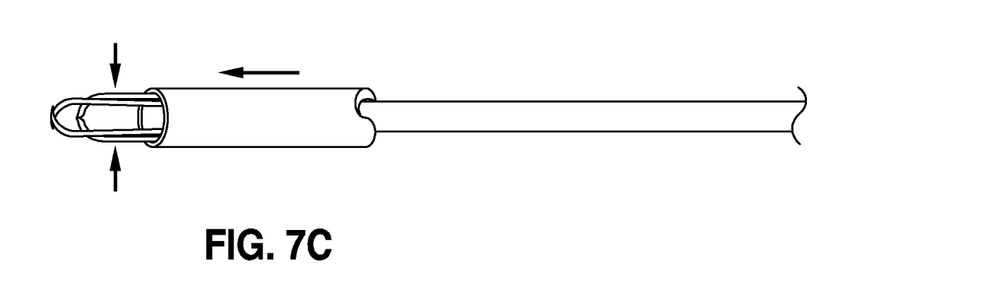

FIGS. 7A-7C show the distal end of another balloon retrieval system 100 which has a dual-wire pair balloon retrieval tool 102. The dual wire pair geometry accomplishes both grasping and cutting depending on the relative position of the tool 102 within the delivery tube 104 lumen. One pair of wires is capable of grasping the intragastric balloon shell, while the second pair of wires—due to their varied geometry—cut through the shell and allow for rapid deflation of the device.

The retrieval tool 102 includes a pair of grasping arms 106 advanced slightly past a pair of cutting arms 108. The grasping arms 106 prevent the sharp cutting arms 108 from being exposed to surrounding tissue. Each grasping arm 106 includes a relatively straight axially-oriented proximal section 110 separated from a distal segment 112 at a bend 113. The terminal end of each of the grasping arms 106 has a grasping hook 114. Each cutting arm 108 also has a relatively straight axially-oriented proximal section 116 separated from a distal segment 118 at a bend 120. Each distal segment 118 further includes an outwardly bent portion 122 that terminates at distal cutting hooks 124. In a preferred embodiment, the inside edges of the outwardly bent portions 122 are sharp to enable cutting of the shell of the intragastric balloon 20. In one embodiment, both pairs of grasping arms 106 and cutting arms 108 are crimped together along the proximal sections 110, 116, such as with a crimping tube 126, or any other means for maintaining wire location and alignment within the instrument lumen.

The balloon retrieval system 100 of FIGS. 7A-7C operates using a three-step procedure. In a first step, the grasping arms 106 and cutting arms 108 are extended from the delivery tube 104 into the open position seen in FIG. 7A, capable of grabbing the device. When the delivery tool 102 retracts partially within the delivery tube 104 lumen, the grasping hooks 114 close, allowing for grasping of the device shell. The geometry of the cutting arms 108 prevents the inner sharp edges from being wholly exposed to surrounding tissue. Complete retraction of the delivery tool 102 within the delivery tube 104 lumen allows the cutting arms 108 to pivot and begin cutting of the intragastric balloon shell, thereby rapidly deflating the device.

Figure 8A:
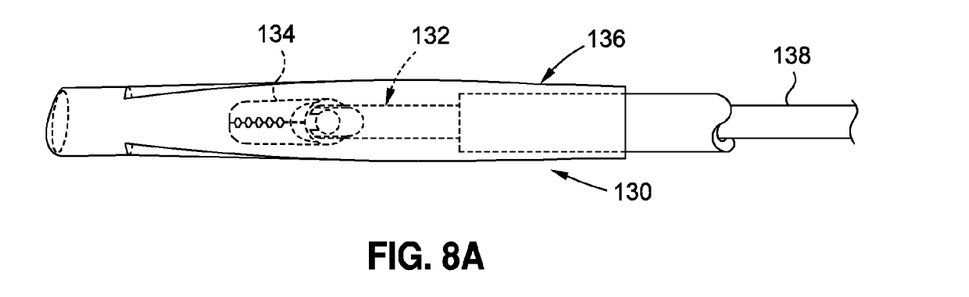
FIGS. 8A-8C are elevational views of a distal end of an alternative balloon retrieval system of the present application having a balloon retrieval tool with grasping jaws that push open cutting blades in a delivery tube in several progressive stages of deployment.
Figure 8B:
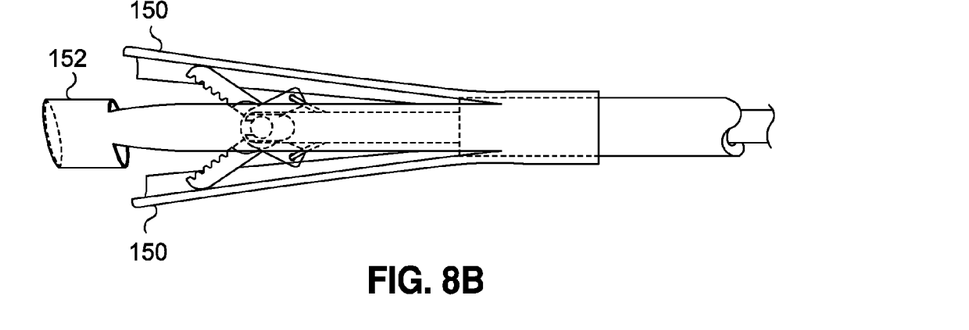
Figure 8C:
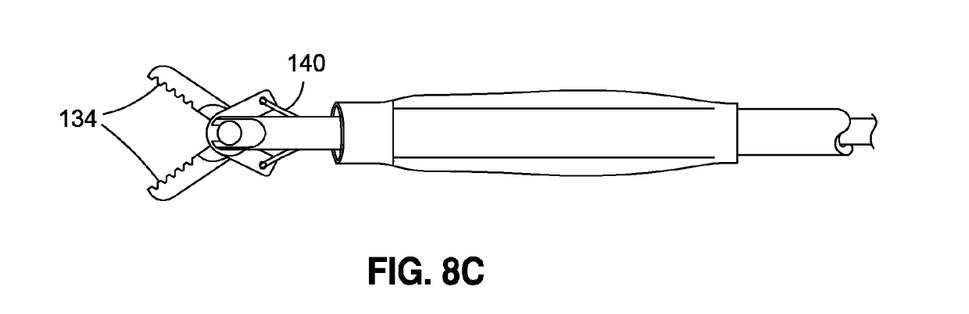

FIGS. 8A-8C illustrate the distal end of an alternative balloon retrieval system 130 having a balloon retrieval tool 132 with grasping jaws 134 that passes through a modified delivery sheath 136. The balloon retrieval tool 132 is substantially similar to earlier graspers, which include an elongated proximal rod 138 terminating in the pair of articulated grasping jaws 134. Displacement of pull wires 140 (see FIG. 8C) manipulates the grasping jaws 134 to open and close.

The modified delivery sheath 136 includes a pair of flexible cutting blades 150 formed in an outer wall thereof. More particularly, the cutting blades 150 may comprise sections of the delivery sheath 136 that are formed by a three-sided rectangle cut in opposite sides of the delivery sheath. A short tubular distal end 152 remains at the end of the delivery sheath. The material of the delivery sheath 136 is such that the blades 150 may flex or be bent outward and then retract or be bent inward to lie substantially flush with the tubular sheath.

Figure 8D:
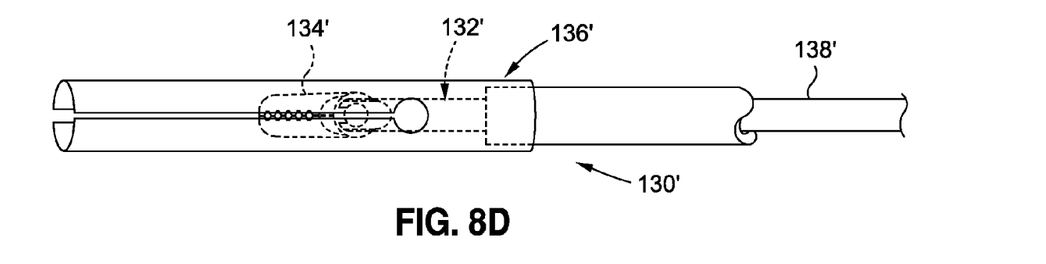
FIGS. 8D-8F are elevational views of a distal end of another balloon retrieval system much like in FIGS. 8A-8C, wherein the grasping jaws push open cutting blades at the distal end of a delivery tube.
Figure 8E:
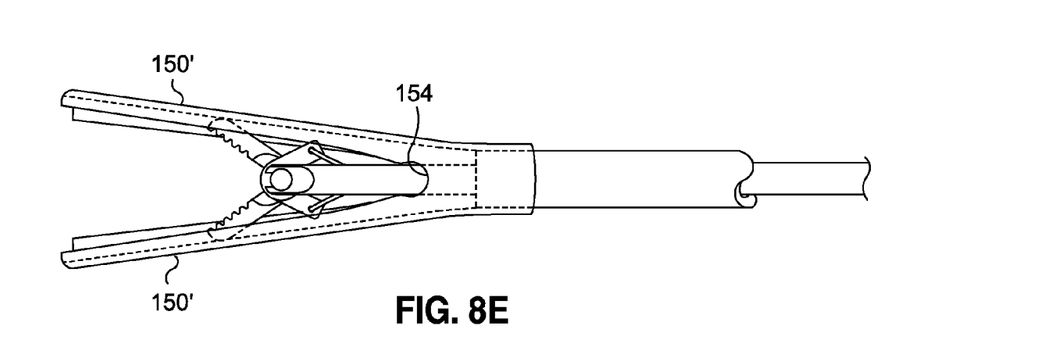
Figure 8F:
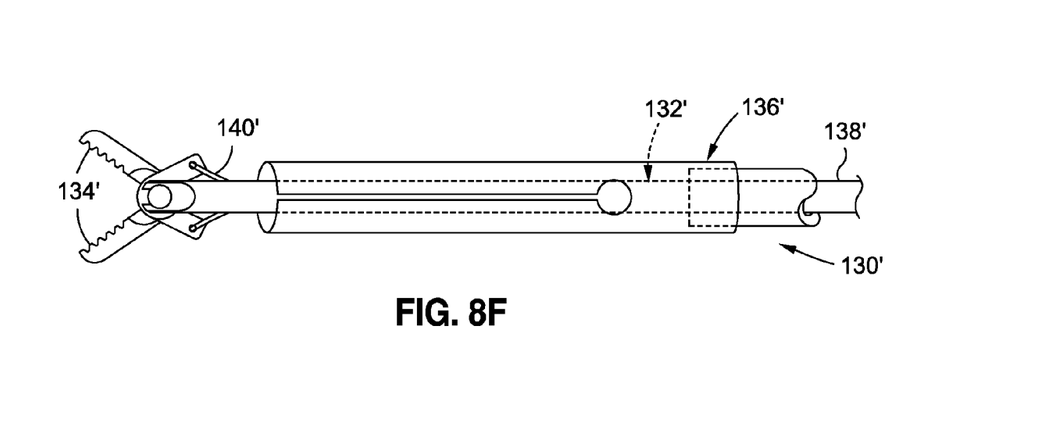

FIGS. 8D-8F show a balloon retrieval system 130' much like the one in FIGS. 8A-8C, having a balloon retrieval tool 132' with grasping jaws 134' that passes through a modified delivery sheath 136'. The balloon retrieval tool 132' includes a proximal rod 138' through which pull wires 140' (see FIG. 8C) pass for manipulation of the grasping jaws 134.

A pair of cutting blades 150' are again utilized to cut the intragastric balloon. Unlike the earlier embodiment, the cutting blades 150' are formed at a distal end of the delivery sheath 136' that may consist of two or more sections created by axial cuts in the sheath. An additional cutout 154 at the proximal end of the blades 150' may exist that reduces the size of each cutting blade's annular cross section, allowing for easier flexing at that point. As before, the material of the delivery sheath 136' is such that the blades 150' may flex or be bent outward and then retract or be bent inward to lie substantially flush with the tubular sheath. Both the retrieval tool 132' and delivery sheath 136' move independently of each other and of an endoscopic device channel (not shown) that the sheath is placed through. When both the retrieval tool and delivery sheath extend out from the channel (FIG. 8D), activation of the retrieval tool 132' causes the cutting blades to open (FIG. 8E). To expose only the retrieval tool 132', the delivery sheath 136' is moved proximal, back into the channel, thereby forcing the blades closed (FIG. 8D). Alternatively, the cutting blades may naturally want to return to their unreformed shape and spring back closed when not being forced open by the retrieval tool.

Figure 9A:
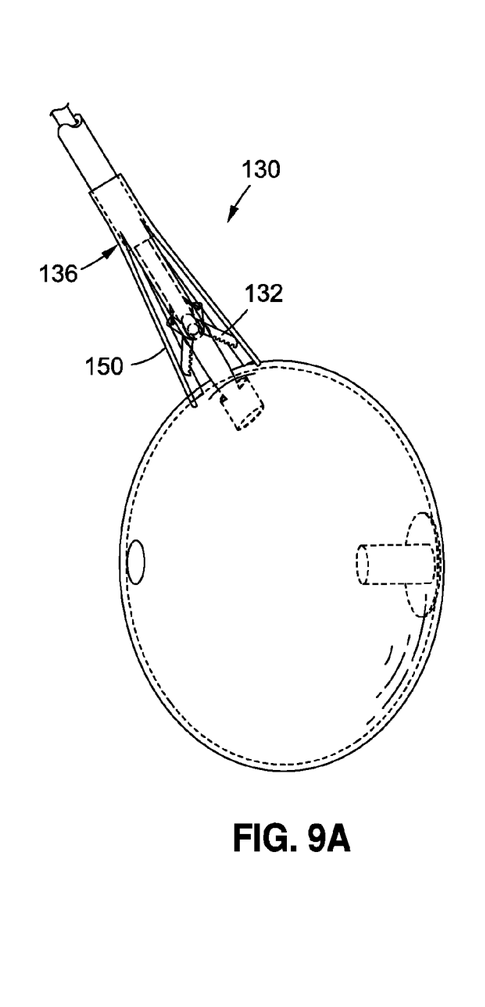
FIGS. 9A-9B are perspective views showing engagement of the balloon retrieval system of FIGS. 8A-8C with an intragastric balloon to effect deflation and removal thereof.
Figure 9B:
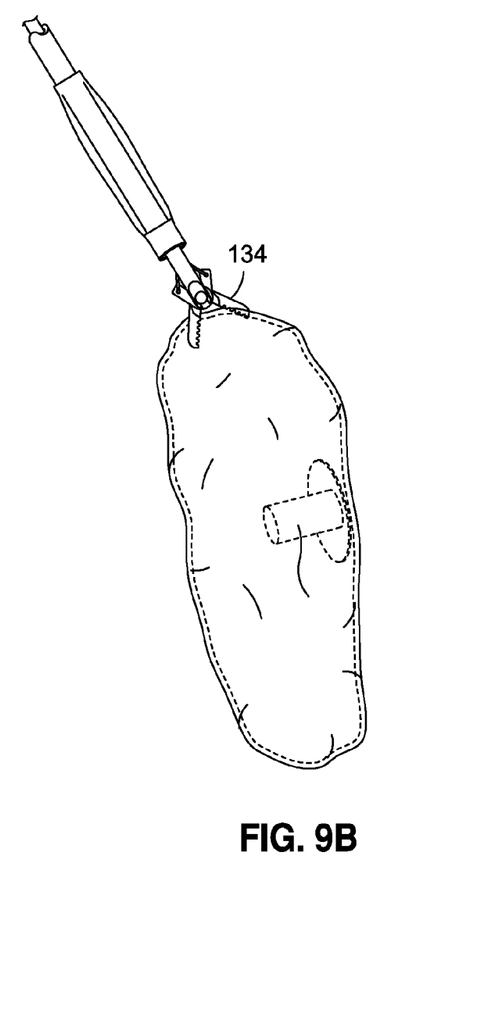

FIGS. 9A-9B are perspective views showing engagement of the balloon retrieval system 130 of FIGS. 8A-8C with an intragastric balloon 20 to effect deflation and removal thereof. First, the balloon retrieval tool 132 is actuated to cause the grasping jaws 134 to open, thus forcing the cutting blades 150 outward from the profile of the delivery sheath 136. The edges of the cutting blades 150 may then be used to cut the shell of the intragastric balloon and deflate the device. Subsequently, the delivery sheath 136 may be refracted within a larger delivery tube (not shown) so that the blades are collapsed—and no longer exposed to tissue—and the grasper is reverted to standard functionality. Alternatively, the cutting blades 150 may resiliently return to the profile of the delivery sheath 136 after closing the grasping jaws 134. Subsequently, the grasping jaws 134 can then be extended past the distal end 152 of the sheath 136 to enable grasping of the deflated intragastric balloon 20.

Figure 10:
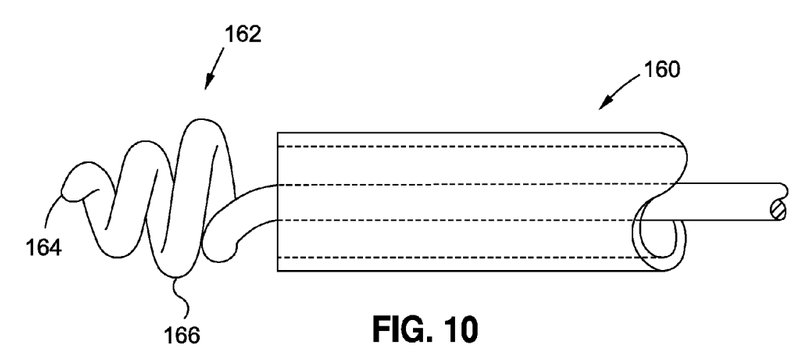
FIG. 10 is an elevational view of a distal end of an exemplary balloon retrieval system having a corkscrew-like balloon retrieval tool.
Figure 11A:
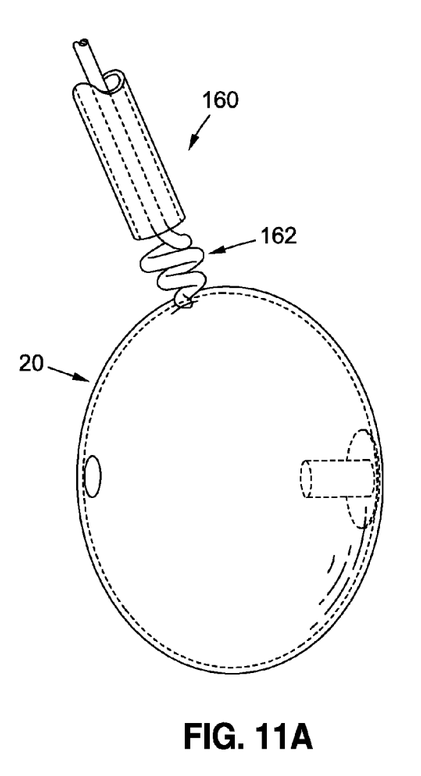
FIGS. 11A-11B are perspective views showing engagement of the balloon retrieval system with an intragastric balloon to effect deflation and removal thereof.
Figure 11B:
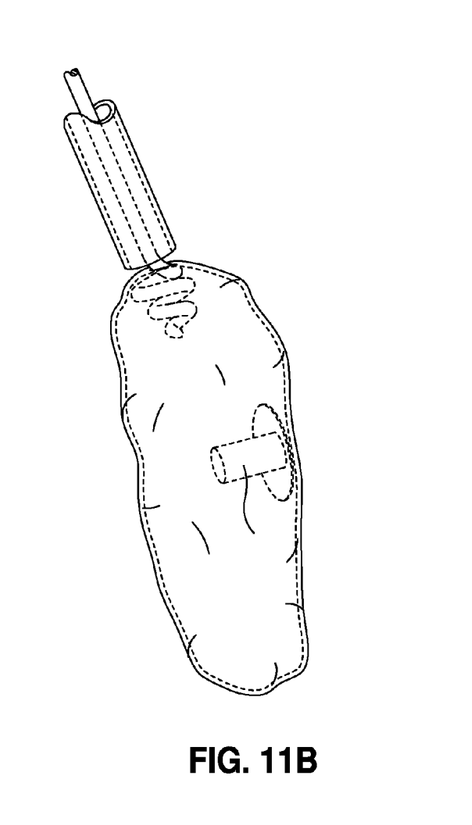

FIG. 10 illustrates an alternative balloon retrieval system 160 having a corkscrew-like balloon retrieval tool 162. FIGS. 11A-11B illustrate engagement of the balloon retrieval system 160 with an intragastric balloon 20 to affect deflation and removal thereof. The retrieval tool 162 can either be a single coiled cork screw type as shown, or a threaded regular screw type (not shown). The retrieval tool 162 includes a sharp or pointed end 164 designed to puncture the silicone shell of the intragastric balloon 20 by rotation when pressed against the shell wall, as seen in FIG. 11A, and a coiled body 166. The coiled body 166 locks and extracts the entire silicone balloon the same way corks are extracted from a wine bottle. A relatively large diameter (width) of the coiled body 166 is desirable for extracting the balloon due to the larger surface area contact of the coil with the internal silicone wall after the coil punctures and enters the interior of the balloon. A larger coiled body 166 can better grab and tug the balloon during the removal process and has less chance of slipping out of the silicone shell. The coiled body 166 can range from cylindrical to cone-shaped geometry (shown in FIG. 10). The sharp or pointed end 164 is desirably covered or protected when not in use so the tool cannot accidentally puncture the stomach linings. Alternatively, the corkscrew geometry may be made of Nitinol, or like shape memory materials, which would allow the design to be fully retracted within the instrument lumen.

Figure 12A:
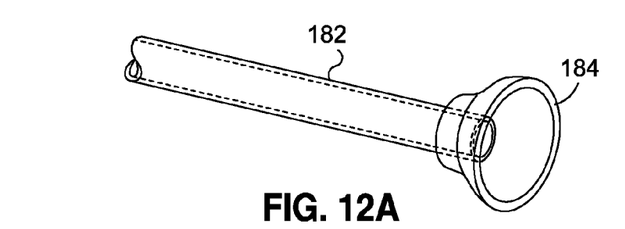
FIGS. 12A-12B are perspective views of a distal end of an alternative balloon retrieval system having suction and a central piercing element.
Figure 12B:
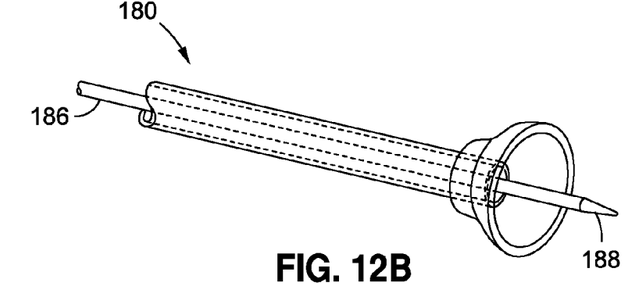
Figure 13A:
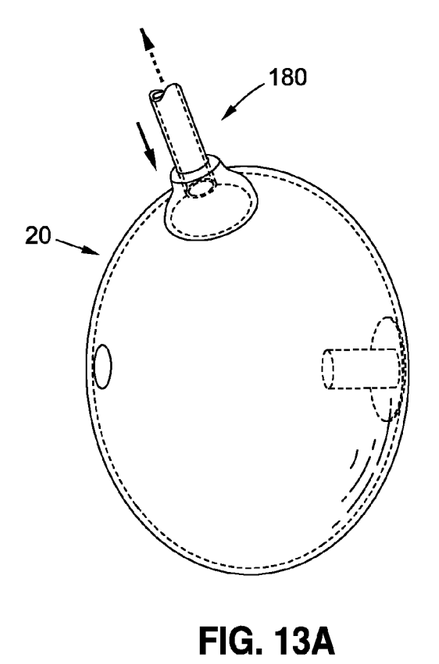
FIGS. 13A-13B are perspective views showing engagement of the balloon retrieval system of FIGS. 12A-12B with an intragastric balloon to effect deflation and removal thereof.
Figure 13B:
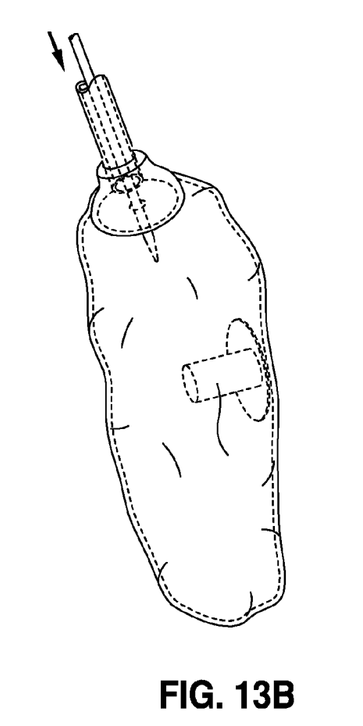

FIGS. 12A-12B show a distal end of a still further balloon retrieval system 180 having suction. More particularly, the system 180 includes an elongated retrieval tube 182 having a suction cup 184 on a distal end thereof. An elongated piercing rod 186 extends through the lumen of the retrieval tube 182 and terminates in a sharpened tip 188. As seen FIGS. 13A-13B the balloon retrieval system first engages an intragastric balloon 20 via suction drawn through the lumen of the tube 182 which causes the suction cup 184 to firmly attach to an exterior wall of the balloon 20. Subsequently, the surgeon displaces the piercing rod 186 distally, thus puncturing the shell of the balloon 20. The same suction or aspiration holding the suction cup 184 to the outside of the balloon facilitates removal of fluid from within the balloon. Alternatively, the piercing rod 186 may include an aspiration channel which can be used to speed up the balloon deflation.

Figure 14A:
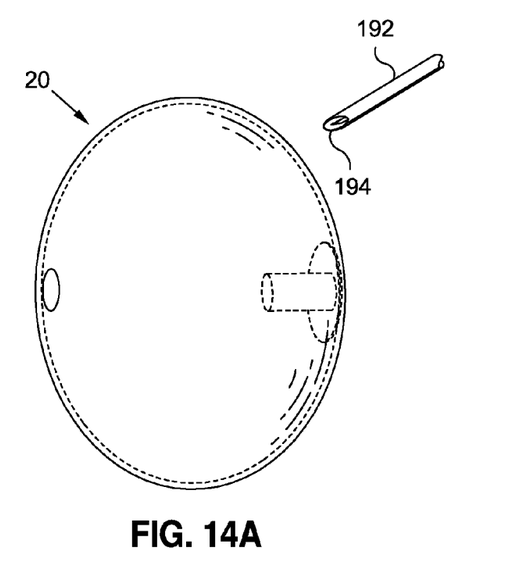
FIGS. 14A-14C are perspective views showing engagement of another balloon retrieval system of the present application having a puncturing needle carrying a pre-formed wireform therein.
Figure 14B:
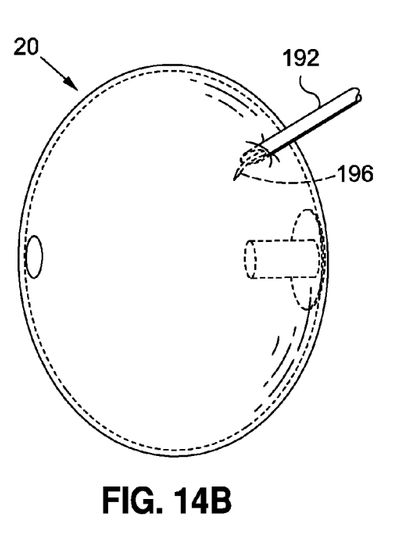
Figure 14C:
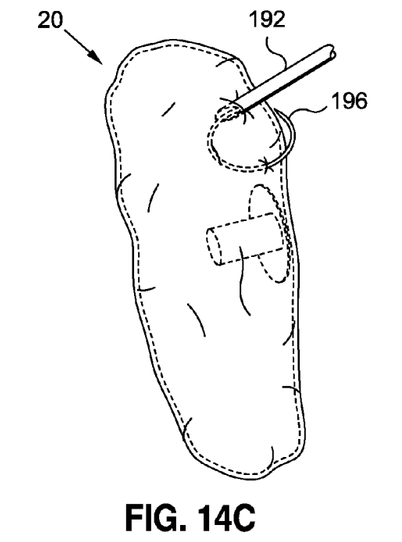

With reference to FIGS. 14A-14C, another balloon retrieval system 190 of the present application includes a puncturing needle 192 having a sharp distal end 194 and a lumen within which slides a pre-formed wireform 196. The needle 192 preferably is connected to a source of suction for aspiration to facilitate deflation of a gastric balloon 20 when punctured by the distal end 194. The pre-formed wireform 196 preferably comprises a shape set Nitinol wire hook which allows grasping of the deflated intragastric balloon shell, while maintaining a lower profile for insertion into the balloon volume. Similar to a fishing hook, the Nitinol wireform 196 geometry provides controllable grasping and puncturing, while still allowing for user controlled release.

In a preferred sequence, the system 190 is introduced down the esophagus down the instrument channel of a visualizing endoscope (not shown), and the surgeon advances the distal end 194 toward the balloon 20, as seen in FIG. 14A, under endoscopic guidance. The sharp distal end 194 then punctures one side of the balloon 20. Subsequently, as seen in FIG. 14B, the surgeon advances the wireform 196 through the lumen of the needle 192; the pre-formed shape of the wireform causing it to curl once expelled from the end 194, as seen in FIG. 14B. Positioning the distal end 194 just inside the shell of the balloon 20 permits the wireform 196 to pierce the shell in a second location, as seen in FIG. 14C, thus emerging from within the balloon. This creates two holes in the balloon 20 which facilitates deflation thereof. Piercing the balloon in this way and curling back on itself enables the wireform 196 to obtain greater purchase on the balloon 20. This allows for more consistent device extractions, at higher pull forces while reducing the likelihood of premature tool release, in contrast with a system in which the wireform remains within the balloon.

The wireform 196 could be expanded to allow for "cinching" of the balloon shell. Since the wireform 196 pierces the shell, it is feasible for the wireform to make a closed loop (not shown completely), that would allow for cinching of the balloon shell. Additionally, it is also possible for the physician to just push the needle 192 up to the balloon 20, then eject the wireform 196 to puncture the balloon by itself.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method for retrieving an intragastric balloon from a stomach of a patient, comprising:
    a) providing an intragastric balloon retrieval tool having an elongated shaft terminating at a coiled body having a pointed end configured to puncture the intragastric balloon;
    b) advancing the retrieval tool through a gastrointestinal tract of the patient to the stomach of the patient;
    c) contacting the coiled body of the retrieval tool against the intragastric balloon within the stomach;
    d) puncturing the intragastric balloon to deflate the intragastric balloon; and e) withdrawing the deflated intragastric balloon from the stomach with the retrieval tool.

2. A method according to claim 1, wherein:
the puncturing includes (i) pressing the pointed end of the coiled body against the intragastric balloon and (ii) rotating the retrieval tool relative to the intragastric balloon.

3. A method according to claim 1, wherein:
the coiled body engages a wall of the intragastric balloon during retrieval.

4. A method according to claim 1, wherein:
the intragastric balloon comprises a silicone wall.

5. A method according to claim 1, wherein:
the coiled body has a cylindrical shape.

6. A method according to claim 1, wherein:
the coiled body has a conical shape.

7. A method according to claim 1, wherein:
the coil body is constructed of a shape memory material.

8. A method for retrieving an intragastric balloon from a stomach of a patient, comprising:
a) providing a system including,
   i) an elongated delivery tube having a lumen, and
   ii) a balloon retrieval tool disposed and able to be longitudinally displaced within the delivery tube lumen, the retrieval tool having an elongated shaft terminating at a helically advanceable element and having a pointed end configured to puncture the intragastric balloon;
b) advancing the system into a gastrointestinal tract to the stomach;
c) puncturing the intragastric balloon within the stomach; and
d) withdrawing the intragastric balloon from the stomach of the patient.

9. A method according to claim 8, wherein:
the helically advanceable element is a coil.

10. A method according to claim 9, wherein:
the coil is constructed of a shape memory material.

11. A method according to claim 9, further comprising:
at least partially retracting the coil into the delivery tube.

12. A method according to claim 8, further comprising:
fully retracting the coil into the delivery tube.

13. A method according to claim 8, wherein:
the puncturing of the intragastric balloon includes rotating the helically advanceable element into the balloon.

14. A method according to claim 13, wherein:
the puncturing of the intragastric balloon further includes rotating the helically advanceable element relative to the delivery tube.

\* \* \* \* \*